US010779753B2

(12) United States Patent
Roosenboom et al.

(10) Patent No.: US 10,779,753 B2
(45) Date of Patent: Sep. 22, 2020

(54) SYSTEM FOR ANALYZING A CONDITION OF AN ANIMAL

(75) Inventors: Derk Jan Roosenboom, Groenlo (NL); Jeroen Martin Van Dijk, Groenlo (NL); Woltherus Karsijns, Groenlo (NL); Egbert Gert Jan Uninge, Groenlo (NL); Jan Anne Kuipers, Groenlo (NL)

(73) Assignee: N.V. NEDERLANDSCHE APPARATENFABRIEK "NEDAP", Groenlo (NL)

( * ) Notice: Subject to any disclaimer, the term of this patent is extended or adjusted under 35 U.S.C. 154(b) by 0 days.

(21) Appl. No.: 14/130,959

(22) PCT Filed: Jul. 5, 2012

(86) PCT No.: PCT/NL2012/050479
§ 371 (c)(1),
(2), (4) Date: Feb. 6, 2014

(87) PCT Pub. No.: WO2013/006056
PCT Pub. Date: Jan. 10, 2013

(65) Prior Publication Data
US 2014/0163406 A1  Jun. 12, 2014

(30) Foreign Application Priority Data

Jul. 5, 2011  (NL) .................................... 2007042

(51) Int. Cl.
*A61B 5/11* (2006.01)
*A01K 11/00* (2006.01)
(Continued)

(52) U.S. Cl.
CPC ........... *A61B 5/1116* (2013.01); *A01K 11/006* (2013.01); *A01K 29/005* (2013.01);
(Continued)

(58) Field of Classification Search
CPC ..... A61B 5/0002; A61B 5/024; A61B 5/1112; A61B 5/1116; A61B 5/1118; A61B 5/113;
(Continued)

(56) References Cited

U.S. PATENT DOCUMENTS 9,044,297 B2*  6/2015  Rajkondawar ....... A01K 29/005
2006/0155172 A1*  7/2006  Rugg .................... A61B 5/1113
600/300

(Continued)

FOREIGN PATENT DOCUMENTS

WO  2007/119070 A1  10/2007
WO  2010/066429 A1  6/2010

*Primary Examiner* — Devin B Henson
(74) *Attorney, Agent, or Firm* — Jacobson Holman PLLC

(57) ABSTRACT

A system for analyzing a condition of an animal, wherein the system includes at least an identification unit (2.1) which is arranged to be worn by an animal, wherein the identification unit includes a first transmitter unit (4), a movement sensor (6), and a control unit (8) which is communicatively connected with the transmitter unit and the movement sensor, wherein the system further includes a receiver unit (8) and a computer (10) which is connected with the receiver unit and wherein the system further includes positioning means for measuring a position of the identification unit, wherein the control unit is arranged for, in use, storing and/or processing electronic information of movements of the animal which have been obtained with the movement sensor. The system is further arranged to feed positions of the identification unit measured with the aid of the positioning means to the computer and/or the control unit, wherein the computer and/or the control unit is arranged to process the electronic information about detected movements and the electronic information about the measured positions in combination for analyzing the condition of the animal.

46 Claims, 4 Drawing Sheets

(51) Int. Cl.
| | |
|---|---|
| *A01K 29/00* | (2006.01) |
| *A61D 17/00* | (2006.01) |
| *A61B 5/024* | (2006.01) |
| *A61B 5/00* | (2006.01) |
| *A61B 5/0245* | (2006.01) |
| *A61B 5/113* | (2006.01) |
| *A61D 99/00* | (2006.01) |

(52) U.S. Cl.
CPC ............ *A61B 5/0002* (2013.01); *A61B 5/024* (2013.01); *A61B 5/0245* (2013.01); *A61B 5/113* (2013.01); *A61B 5/4368* (2013.01); *A61D 17/002* (2013.01); *A61D 17/006* (2013.01); *A61D 17/008* (2013.01); *A61D 99/00* (2013.01)

(58) Field of Classification Search
CPC .. A61B 2503/40; A61D 17/00; A61D 17/002; A61D 17/006; A61D 17/008; A01K 11/006; A01K 11/008; A01K 29/005; G06F 19/3418
See application file for complete search history.

(56) References Cited

U.S. PATENT DOCUMENTS

| | | | |
|---|---|---|---|
| 2007/0130893 A1* | 6/2007 | Davies ................ | A01K 11/008 54/1 |
| 2010/0030036 A1* | 2/2010 | Mottram ................ | A01K 11/00 600/301 |
| 2010/0198024 A1* | 8/2010 | Elazari-Volcani ........................... | G06F 19/3418 600/301 |
| 2010/0302004 A1* | 12/2010 | Winstead ............ | A01K 29/005 340/7.32 |
| 2011/0298619 A1* | 12/2011 | O'Hare ................ | A01K 11/008 340/573.1 |

* cited by examiner

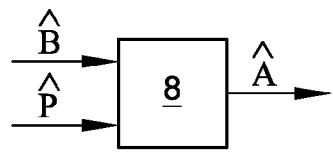 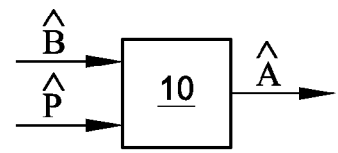
Fig. 2A　　　　　　　　Fig. 2B
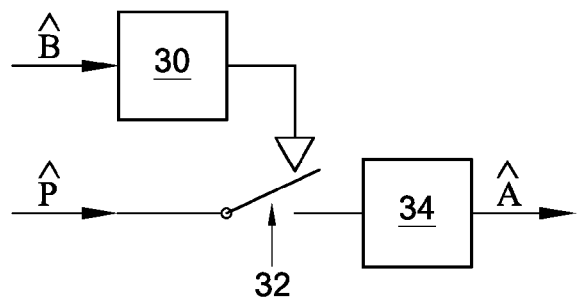
Fig. 3
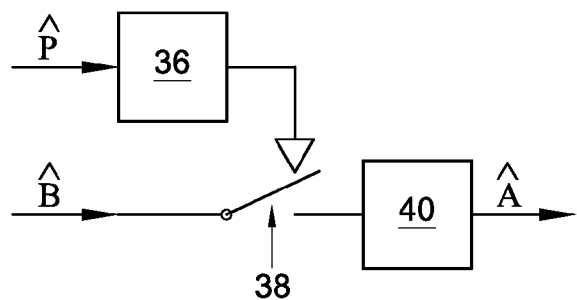
Fig. 4A
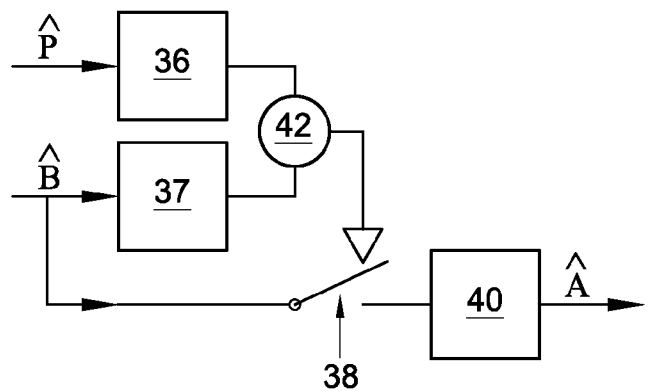
Fig. 4B

SYSTEM FOR ANALYZING A CONDITION OF AN ANIMAL

This is a national stage of PCT/NL12/050479 filed Jul. 5, 2012 and published in English, which has a priority of The Netherlands no. 2007042 filed Jul. 5, 2011, hereby incorporated by reference.

The invention relates to a system for analyzing a condition of an animal, wherein the system includes at least an identification unit which is arranged to be worn by an animal, wherein the identification unit includes a first transmitter unit, a movement sensor, and a control unit which is communicatively connected with the transmitter unit and the movement sensor, wherein the system further includes a receiver unit and a computer which is connected with the receiver unit and wherein the system further includes positioning means for measuring a position of the identification unit, wherein the control unit is arranged for, in use, storing and/or processing electronic information of movements of the animal which have been obtained with the movement sensor, and wherein the control unit is possibly arranged to transmit electronic information about the detected movements of the animal and/or an identification code which is stored in the identification unit with the aid of the transmitter unit to the receiver unit, wherein the receiver unit feeds the received electronic information about the detected movements and/or the identification code to the computer. Such systems are known per se. In the known system the positioning means can consist, for example, of a GPS receiver which is included in the identification unit. The positioning means can thus determine the position of the identification unit. The determined position can then, for example, be transmitted with the aid of the transmitter unit and be received by the receiver unit for registration of positions of the animal with the aid of the computer. A drawback of the known system is that the processing of electronic information of the movements of the animal in order to analyze the condition of the animal is difficult. In particular, it is difficult to recognize mutually different conditions of the animal, since these different conditions nonetheless involve comparable movements of the animal.

The invention contemplates the provision of a system in which analyzing can be improved and expanded. The system according to the invention is characterized in that the system is further arranged to feed positions of the identification unit measured with the aid of the positioning means to the computer and/or the control unit, wherein the computer and/or the control unit is arranged to process the electronic information about detected movements and the electronic information about the measured positions in combination for analyzing the condition of the animal, wherein, if the control unit is arranged to process the electronic information about detected movements and the electronic information about the measured positions in combination, the control unit is preferably also arranged to transmit information about the result of the analysis with the transmitter unit to the receiver unit for storage and/or further processing in the computer. Owing to the electronic information about the detected movements and the electronic information about the measured positions being processed in combinations, analyzing of the condition of an animal can be improved. In particular, it holds that the computer and/or the control unit is arranged to interpret the electronic information about detected movements in dependence upon the electronic information about the measured positions. Also, it may hold, in particular, that the computer and/or the control unit is arranged to interpret the electronic information about measured positions in dependence upon the electronic information about the detected movements. According to a practical embodiment, it holds that the computer and/or the control unit is arranged to select on the basis of the electronic information about the detected movements and/or on the basis of the electronic information about the measured positions a predetermined filter and/or a predetermined algorithm with which the electronic information about the measured positions and/or the electronic information about the detected movements is processed. More particularly, it holds here that the computer and/or the control unit is arranged to select on the basis of the electronic information about the detected movements the predetermined filter and/or the predetermined algorithm for processing electronic information about the measured positions. Also, instead, or additionally, it may hold that the computer and/or the control unit is arranged to select on the basis of the electronic information about the measured positions the predetermined filter and/or the predetermined algorithm for processing the electronic information about the detected movements. The system according to the invention may, for example, be arranged such that the computer and/or the control unit is arranged to be able to conclude on the basis of the electronic information about the detected movements whether the animal is walking or not walking and to process the electronic information about the measured positions with a first predetermined filter and/or a first predetermined algorithm if the animal is not walking (e.g., is lying or standing).

Also, it is possible, for example, that the computer and/or the control unit is arranged to recognize on the basis of the electronic information about the measured positions of the animal that the animal is in a bedded area and to process the electronic information about the detected movements of the animal with a second predetermined filter and/or a second predetermined algorithm if it has been recognized that the animal is in the bedded area and optionally provided that it has additionally been recognized on the basis of the electronic information about the measured movements of the animal that the animal is lying or standing still, with the second predetermined filter being arranged to pass predetermined movements which are associated with rumination and/or with the second predetermined algorithm being arranged to recognize predetermined movements which are associated with rumination.

The invention will be further elucidated with reference to the drawings, in which:

FIGS. 2A and 2B show possible exemplary embodiments of the invention according to FIG. 1; and FIG. 3-FIG. 17 show possible exemplary embodiments for the operation of the control unit and/or the computer of FIG. 1.

Figure 1:
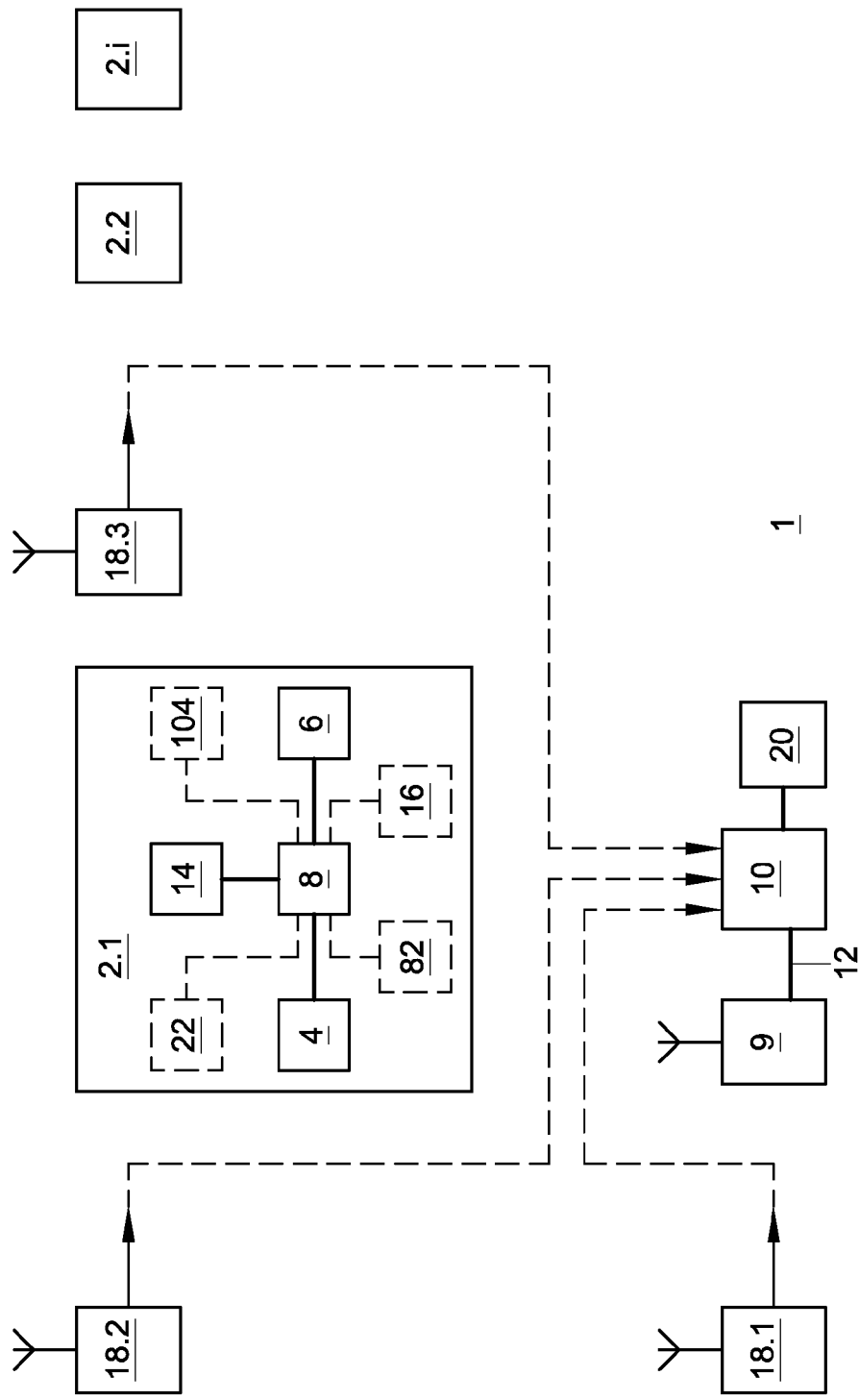
FIG. 1 shows a possible embodiment of a system according to the invention.

In FIG. 1 a system according to the invention is denoted with reference numeral 1. The system includes an identification unit 2.1 which is arranged to be worn by an animal. The identification unit may, for example, be attached to a strap in order to attach the identification unit around the neck of an animal such as a cow. The identification unit may, for example, be attached so as to abut against the neck of an animal. In this example, the identification unit includes a first transmitter unit 4, a movement sensor 6, and a control unit 8 which is communicatively connected with the transmitter unit 4 and the movement sensor 6. The first transmitter unit may be implemented, for example, as a UHF transmitter. The movement sensor may be implemented, for example, as an acceleration detector (G-sensor), compass, gyroscope or other movement sensor.

The system further includes a receiver unit 9 and a computer 10 which is communicatively connected with the receiver unit 9, in this example via a cable 12.

The system further includes positioning means for measuring a position of the identification unit 2.1. The positioning means in this example are formed by a GPS receiver 14 which is part of the identification unit 2.1 and which is communicatively connected with the control unit 8. In this example, it holds that the GPS receiver 14 feeds electronic information about the measured position to the control unit 8. Now, for example, there may be two situations. The control unit 8 is arranged to process the electronic information $\hat{B}$ about the detected movements and the electronic information $\hat{P}$ about the measured positions in combination for analyzing the condition of an animal. The control unit 8 can cause the result of these processing operations $\hat{A}$, i.e., the result of the analysis, to be transmitted with the transmitter unit to the receiver unit 9. The receiver unit 9 then sends the received results of the analysis via the cable 12 to the computer 10 for further processing and/or storage in the computer.

It is also possible, however, that the control unit 8 is arranged to transmit the electronic information about detected movements of an animal obtained with the aid of the movement sensor 6 with the aid of the transmitter unit to the receiver unit 9. The receiver unit 9 feeds the received electronic information about detected movements via the cable 12 to the computer 10. Also, the control unit 8 causes electronic information about measured positions of the identification unit obtained with the aid of the GPS receiver to be transmitted with the aid of the transmitter unit 4. The electronic information about the measured positions received with the aid of the receiver unit is likewise fed via the cable 12 to the computer 10. In that case, for example, the computer may be arranged to process the electronic information about detected movements and the electronic information about the measured positions in combination for analyzing the condition of the animal. Such analysis can hence, according to the invention, be carried out by the control unit 8 and/or be carried out by the computer 10.

It holds that the computer and/or the control unit is arranged to process the electronic information about detected movements and the electronic information about the measured positions in combination for analyzing the condition of the animal.

If the electronic information about the measured positions $\hat{P}$ and the electronic information about detected movements $\hat{B}$ are processed in combination by the control unit, the control unit is preferably also arranged to transmit information about the result $\hat{A}$ of the analysis with the aid of a transmitter unit to the receiver unit for storage and further processing in the computer.

It is noted that the positioning means may also be implemented in a different manner. Thus, it is conceivable, for example, that the identification unit 2.1 is provided with a second transmitter unit 16 with which an electromagnetic signal is transmitted. Furthermore, the system may then include, for example, a plurality of receiver units 18.$i$ ($i=1$, $2, 3, \ldots n$), with $n=3$ in this example. The receiver units 18.$i$ are set up at mutually different predetermined positions. The receiver units 18.$i$ receive the signal transmitted by the transmitter 16. The receiver units 18.$i$ transfer this information via a communicative connection with the computer to the computer 10. On the basis of this information the computer 10 can calculate in a known manner what the position is of the transmitter 16 and hence the position of the identification unit 2.1. Thus, the computer calculates electronic information $\hat{P}$ about the position of the identification unit. If the signal transmitted by the transmitter unit 16 is pulsed, this position can be determined, for example, on the basis of differences in transmission time from the transmitter to the various receivers 18.$i$. Also, if a continuous wave signal is transmitted by the transmitter 16, the position of the transmitter unit 16 can be calculated on the basis of phase differences between the signals received with the aid of the receivers 18.$i$. In this example, such a calculation can be carried out with the aid of the computer. If the computer, as described above, processes the electronic information $\hat{P}$ about measured positions and the electronic information $\hat{B}$ about detected movements in combination, it is merely needed that the control unit 8 feeds the electronic information about the detected movements of the animal with the aid of a transmitter unit 4 via the receiver 9 to the computer 10. If, however, it is intended that the control unit 8 processes the electronic information about detected movements and the electronic information about the measured positions in combination, the system may be arranged such that the computer 10, on the basis of the signals received by the receivers 18.$i$, determines electronic information $\hat{P}$ about the position of the identification unit 2.1. The computer 10 can then feed this electronic information $\hat{P}$ to a transmitter unit 20 coupled with the computer. The identification unit 2.1 may, in that example, further include a separate receiver 22 for receiving the transmitted electronic information $\hat{P}$ about the measured positions. The receiver 22 feeds the received information $\hat{P}$ about the measured position to the control unit 8. The control unit 8 can thus process the electronic information $\hat{B}$ about the detected movements, obtained with the aid of the movement sensor 6, and the electronic information $\hat{P}$ about the measured positions in combination for analyzing the condition of the animal.

It is also possible that the computer feeds the signals obtained from the receivers 18.$i$ to the transmitter 20. The receiver 22 thereupon receives these signals and feeds them to the control unit 8. In that case, the control unit 8 itself calculates the electronic information $\hat{P}$ about the position of the identification unit 2.1 from the received signals.

As indicated above, it holds, therefore, that the control unit 8 can be fed with electronic information about detected movements $\hat{B}$ and electronic information about measured positions $\hat{P}$ to process them in combination for analyzing the condition of an animal to obtain an analysis result $\hat{A}$, as shown in FIG. 2A. Further, it is possible that the electronic information about detected movements $\hat{B}$ and the electronic information about measured positions $\hat{P}$ is fed to the computer 10 to process this information in combination for analyzing a condition of the animal and to obtain an analysis result $\hat{A}$ as shown in FIG. 2B. Both possibilities can be carried out alone or in combination. In the following, a number of examples will be given of processing operations that can be carried out by the control unit 8 and/or by the computer 10. The examples that are given hereinafter can also be carried out parallel to each other. A first example is discussed with reference to FIG. 3. For this example, it holds that the computer and/or the control unit is arranged to conclude on the basis of the electronic information about the detected movements $\hat{B}$ whether the animal is walking or not walking. This can be carried out, for example, by feeding the electronic information about the detected movements $\hat{B}$ to a filter 30 which has the property of delivering a signal when the animal is not walking. The result is that the switch 32 is closed by an output signal of the filter. Closure of the switch has as a result that the electronic information $\hat{P}$ about the positions of an animal is fed to a first predetermined filter 34. The filter 34 may be arranged so as to integrate the electronic information about the measured positions, so that the electronic information is averaged in time. In this manner, when the animal is standing still or lying, an accurate positioning can be carried out. The filter 30 and the filter 34 can be implemented both in hardware and in software. Also, it is possible that the electronic information about the measured positions of the animal, instead of being processed with a hardware filter 34, is processed with a first predetermined algorithm 34 if the animal is not walking. In FIG. 3 this predetermined algorithm is also denoted schematically with the reference numeral 34. In fact, a software filter corresponds to a predetermined algorithm for the processing of the electronic information about the positions $\hat{P}$ measured spread in time. Entirely analogously, the filter 30 may also be replaced with a predetermined algorithm. It is noted that the switch 32 can be implemented both in hardware and as software.

Another example is discussed with reference to FIG. 4A. For this example, it holds that the computer and/or the control unit is arranged to recognize on the basis of the electronic information about the measured positions $\hat{P}$ that the animal is in a bedded area. Such recognition can be carried out with the aid of a predetermined algorithm 36 or a filter 36. If it is recognized that the animal is in the bedded area, the switch 38 is closed. This has as a result that the electronic information about the detected movements $\hat{B}$ of the animal is processed with a third filter 40 or a third predetermined algorithm 40. The third predetermined filter is arranged to pass predetermined movements which are associated with rumination. If not a filter but a predetermined algorithm 40 is used, it holds that this third predetermined algorithm is arranged to recognize predetermined movements which are associated with rumination.

In FIG. 4B a slightly refined embodiment of the variant according to FIG. 4A is shown. Corresponding parts are provided with the same reference numeral. With the aid of the filter 36 or the predetermined algorithm 36 it is determined whether the animal is in the bedded area. Also, on the basis of the electronic information about the detected movements $\hat{B}$ of the animal, it is determined with the aid of a filter 37 and/or a predetermined algorithm 37 whether the animal is lying or standing still. If the animal is lying or standing still, this is passed on to the summator 42 with a logic 1. If the animal is in the bedded area, this is likewise passed on to the summator 42 with a logic 1 by the filter 36 or by the predetermined algorithm 36. Only when both conditions are satisfied, i.e., the animal is in the bedded area and the animal is lying or standing still, is the switch 38 closed. The processing of the electronic information about the measured movements of an animal with the second predetermined algorithm 40 and/or the second predetermined filter is wholly analogous to the processing as discussed with reference to FIG. 4A. It is noted that the switch 38 and the summator 42 may be implemented as software and in hardware. This also holds for the switches to be discussed hereinafter.

Figure 5:
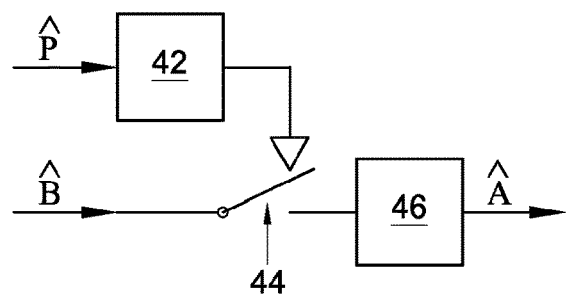

In the example of FIG. 5 it holds that the computer and/or the control unit is arranged to recognize on the basis of the electronic information about the measured positions of the animal that the animal is in a predetermined area in a feeding space. Such recognition can be carried out with the aid of an electronic filter 42 and/or a predetermined algorithm 42. If it is recognized that the animal is in a predetermined area in a feeding space, the switch 44 is closed. The result is that the electronic information $\hat{B}$ about the detected movements of the animal is processed with a third predetermined filter 46 and/or a third predetermined algorithm 46. The third predetermined filter 46 is arranged to pass predetermined movements which are associated with eating as analysis result $\hat{A}$. The third predetermined algorithm 46 is arranged to recognize predetermined movements which are associated with eating. If such a movement is recognized, for example, a logic 1 may be delivered as analysis result $\hat{A}$. In particular, it holds that the control unit and/or the computer is further arranged to register, on the basis of the electronic information passed by the third predetermined filter 46 and/or movements recognized with the third predetermined algorithm, the length of an eating time, the number of eating sessions and/or the times at which eating is done.

Figure 6:
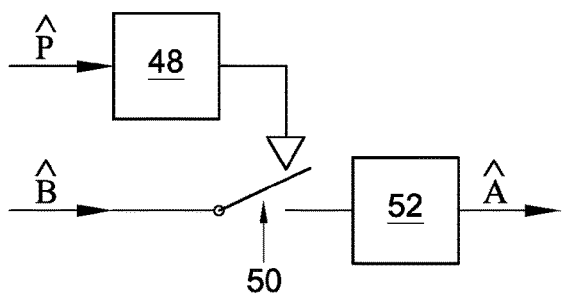

According to FIG. 6 the computer and/or the control unit is arranged to recognize on the basis of the electronic information $\hat{P}$ about the measured position of the animal that the animal is in a walking space. Such recognition can be carried out with the aid of a predetermined filter 48 and/or predetermined algorithm 48. If it has been recognized that an animal is in the walking space, the switch 50 is closed. This has as a result that the electronic information $\hat{B}$ about the detected movements of the animal is processed with a fourth predetermined filter 52 and/or a fourth predetermined algorithm 52. It holds here that the fourth predetermined filter is arranged to pass predetermined movements which are associated with estrus of the animal. Such passed movement is then an analysis result $\hat{A}$. Also, it holds that the fourth predetermined algorithm 52 is arranged to recognize predetermined movements which are associated with estrus of the animal. If such a movement is recognized, this is indicated, for example, by outputting the analysis result $\hat{A}$ as logic 1. If the analysis according to FIG. 6 is carried out by the control unit, the result thereof is transmitted with the aid of the transmitter 4 and, after reception with the receiver 9, fed to the computer 10. Also, it may be that the analysis in question is carried out with the computer, as a result of which the analysis result $\hat{A}$ is already known at the computer as it is. For both variants it holds, in particular, that the computer may be arranged to register where the animal is located at the moment that movements associated with estrus of the animal are detected in respect of this animal. The computer may furthermore be arranged to determine for other animals each also provided with an identification unit 2.$i$ (i=2, 3, . . . n) when they have been in the neighborhood of an animal in respect of which movements associated with estrus of the animal have been detected. Evidently, to this end, it is necessary that the electronic information about the measured positions $\hat{P}$ is passed on by the identification units to the computer with the aid of the transmitter units 4 of the identification unit. By thus registering with the aid of the computer where an increased activity of the animals has been observed, followers (animals that may not be estrous but are prompted by another animal and as a result have an increased activity) can be identified. It is known which animals were together at that moment. With the aid of calendar data of the animals, the right animal can be reported estrous. In this way, the number of false-positive reports is lowered.

Figure 7:
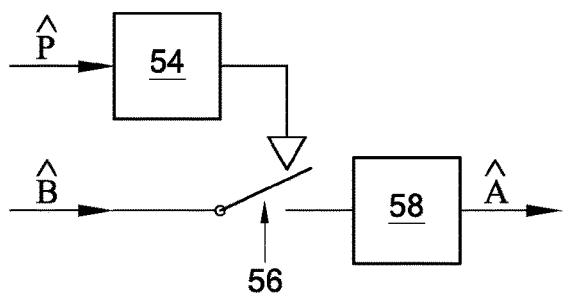

According to FIG. 7 the computer and/or control unit is arranged to recognize on the basis of the electronic information about the measured positions $\hat{P}$ of the animal that the animal is in a calving pen. Such recognition can be carried out with the aid of a predetermined filter 54 and/or a predetermined algorithm 54. If it has been recognized that the animal is in a calving pen, the switch 56 is closed. When the switch 56 is closed, the electronic information about the detected movements of the animal is processed with a fifth predetermined filter 58 and/or a fifth predetermined algorithm 58. It holds here that the fifth predetermined filter is arranged to pass predetermined movements which are associated with the calving of the animal. These passed movements are then the analysis result Â. Furthermore, it holds that the fifth predetermined algorithm is arranged to recognize predetermined movements which are associated with calving of the animal. The predetermined movement which is associated with calving can consist, for example, of repeated lying down and getting up again. When the fifth predetermined algorithm recognizes such a movement, for example, a logic 1 can be outputted as analysis result Â. This analysis result, like the earlier-mentioned analysis results, may be registered by the computer, for example, in combination with the identity of the animal and the moment at which the analysis result is valid.

Figure 8:
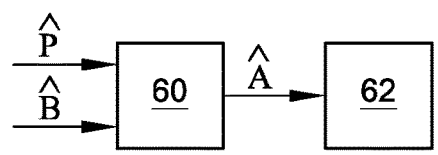

According to FIG. 8 the computer 10 and/or the control unit 8 of FIG. 1 is arranged to recognize on the basis of the electronic information B̂ about successively measured positions of the animal and on the basis of the electronic information about the detected movements of the animal whether an animal takes steps of a length that is less than a predetermined length. Such recognition can be carried out with the aid of a predetermined algorithm 60. The analysis result Â of the algorithm 60 can be, for example, a logic 1 when the animal takes steps of a length that is less than a predetermined length. Each logic 1 that is generated as an analysis result can, for example, correspond to such a step. The moment at which the logic 1 is generated corresponds to the moment at which the respective step is taken. Preferably, it holds that the computer and/or the control unit is arranged to generate an alert signal when the computer and/or control unit has recognized a multiplicity of steps of a length that is shorter than the predetermined length. To this end, the computer and/or the control unit may be provided with a second algorithm 62 which detects when, as analysis result Â, in succession a number of logic is are detected. This second predetermined algorithm 62 then causes the alert signal to be generated.

Preferably, it holds that the control unit is arranged such that the frequency with which the electronic information about the position of the animal is transmitted by the transmitter unit 4 depends on the electronic information about the detected movements of the animal. More particularly, it holds here that the control unit is arranged so as to cause the frequency to be relatively low when the control unit concludes on the basis of the electronic information about the detected movements that the animal is standing still or lying. Also, it is possible that the control unit is arranged so as to cause the frequency to be relatively high when the control unit concludes on the basis of the electronic information about detected movements that the animal is walking.

Figure 9:
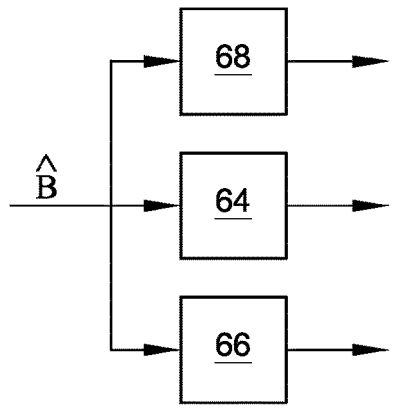

As shown in FIG. 9, with the aid of a predetermined algorithm or filter 64 it can be determined that the animal is standing still or lying and with the aid of a predetermined algorithm or filter 66 it can be determined that the animal is walking. When with the aid of the predetermined algorithm or filter 64 it is determined that the animal is lying or standing still, the frequency referred to becomes relatively low, and when with the aid of the predetermined algorithm or filter 66 it is determined that the animal is walking, the frequency is set to be relatively high.

Also, the control unit may further be arranged to carry out a fourth predetermined algorithm or filter 68. This is also represented in FIG. 9. This fourth algorithm causes the frequency to be lowered or increased when the control unit on the basis of the electronic information about detected movements concludes that the animal is going to move less, or more, respectively. So, if the animal moves fast, the frequency of transmission is raised so that the position of the animal can be accurately followed. When the animal moves less, the frequency for transmission may be lowered so that even at the lowered frequency the position of the animal can still be accurately followed. Of course, this concerns a variant where the position of the animal is transmitted with the aid of the transmitter unit with the frequency referred to.

Figure 10:
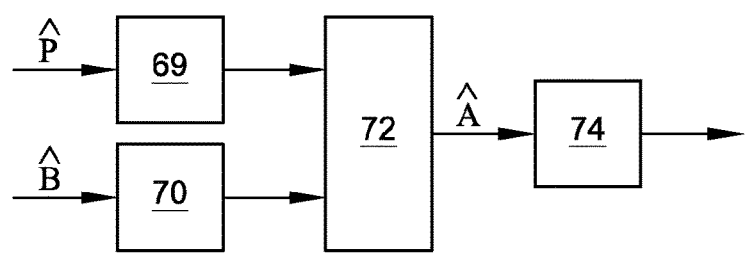

According to FIG. 10 the computer and/or the control unit is arranged to recognize on the basis of the electronic information about the measured position P̂ of the animal that the animal is in a cubicle. Such recognition can be carried out with the aid of a predetermined algorithm or filter 69. Furthermore, it holds that the computer and/or the control unit is arranged to recognize on the basis of the electronic information B̂ about the detected movements of the animal that the animal is lying. This can be carried out with the aid of a predetermined algorithm or filter 70. Furthermore, the computer and/or the control unit are arranged to register that the animal is lying when on the basis of the electronic information about the measured position of the animal it has been recognized that the animal is in the cubicle and on the basis of the electronic information about the detected movements of the animal it has been recognized that the animal is lying. This can be carried out with the aid of the algorithm or the filter 72. In this manner it can be established with certainty when the animal is lying. The analysis result Â then concerns the times at which the animal is lying. Preferably, it holds furthermore that the computer and/or the control unit are further arranged to register lying times of the animal on the basis of the registered information about the lying of the animal, where 'lying times' can be understood to mean the times at which the animal is lying and/or the length of the periods during which the animal is lying. This last can be carried out, for example, with a predetermined algorithm 74.

Figure 11:
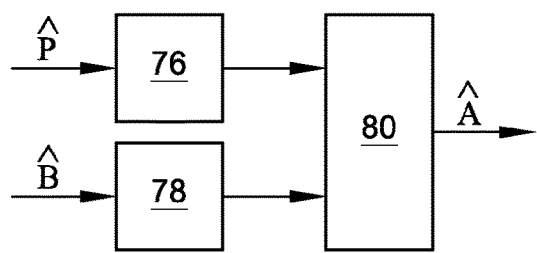

According to FIG. 11 the computer and/or control unit is also arranged to recognize on the basis of the electronic information P̂ about the measured position of the animal that the animal is not in a cubicle. This can be carried out, for example, with the predetermined algorithm or filter 76. Furthermore, it holds that the computer and/or the control unit is arranged to recognize on the basis of the electronic information B̂ about the detected movements of the animal, that the animal is lying. This can be carried out with the aid of a predetermined algorithm or filter 78. Also, it holds that the computer and/or the control unit is arranged to register that the animal is one tending to lie down not in a cubicle but elsewhere, called a 'damslaper' in Dutch, hereinafter generally and informally referred to as 'off-bedding sleeper', when on the basis of the electronic information about the measured position of the animal it has been recognized that the animal is not in the cubicle and on the basis of the electronic information about the detected movements of the animal it has been recognized that the animal is lying. This can be carried out, for example, with the aid of a predetermined algorithm or filter 80. The analysis result Â is then that the animal with a particular identity ID is an off-bedding sleeper. It is noted here that the identification unit 2.1 may be provided with an identification code. This identification code is then related to the identity of the animal. It is possible that the identification code is stored in the control unit 8 and can be transmitted with the aid of the transmitter 4 to the computer 10.

If it appears that the animal is an off-bedding sleeper, the system may further include means of stimulating the animal. These means can consist, for example, of a unit 82 of the identification unit 2.1 which can be activated with the control unit 8 to apply an electrical stimulus to the neck of the animal. This can be simply carried out when the control unit is arranged to determine whether an animal is an off-bedding sleeper. When the computer is arranged to determine whether an animal is an off-bedding sleeper, the computer can transmit a signal via the transmitter 20, which is received by the receiver 22, after which the control unit 8 can activate the unit 82.

Figure 12:
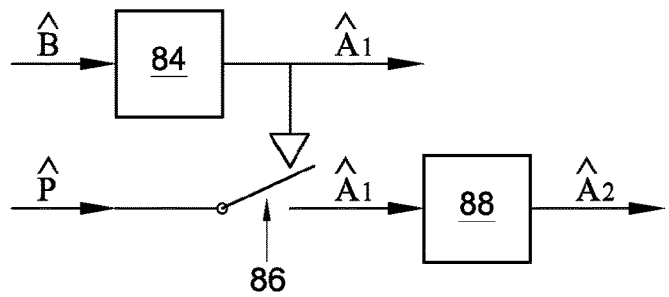

According to FIG. 12 the computer and/or the control unit is arranged to recognize on the basis of the electronic information $\hat{B}$ of the animal that the animal is restless. The restlessness of the animal is accompanied by a multiplicity of movements in a relatively short time. This can be recognized with the aid of the predetermined algorithm or filter 84. When it is determined that the animal is restless, the switch 86 is closed so that also the position can be determined when the animal is restless. The position when the animal is restless is the analysis result $\hat{A}$. Preferably, it holds that the control unit and/or computer is further arranged to generate an alert signal when it recognizes that the animal is restless and/or to register each time where the animal is when it is restless. This last can be carried out with the aid of a predetermined algorithm 88. In particular, for each identification unit 2.1 the analysis according to FIG. 12 is carried out. This can then be carried out by the control unit of the respective identification unit or by the computer which receives the relevant information for carrying out the algorithm according to FIG. 12 from the respective identification unit. The system can then be further arranged to recognize that a plurality of the animals are restless and where the restless animals are then located. Preferably, it holds that the system is further arranged to generate an alert signal when it has been recognized that restless animals are in the vicinity of each other and/or to register each time where the animals are located when they are restless. This last can then be carried out by an algorithm with the aid of the computer.

Figure 13:
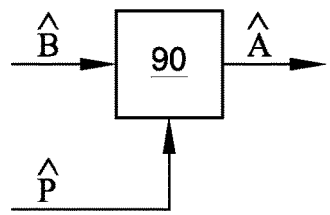

According to FIG. 13 it holds that the computer and/or the control unit is arranged to recognize on the basis of electronic information about the detected movements $\hat{B}$ of the animal that the animal is standing still and to register when and how long the animal is standing still, preferably together with information on where animal is standing still then. All this can be carried out with the aid of the algorithm 90.

Figure 14:
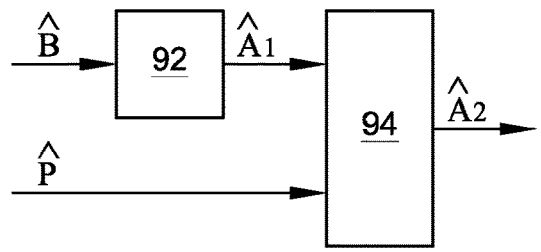

According to FIG. 14 it holds that the computer and/or the control unit is arranged, on the basis of the electronic information $\hat{B}$ about the detected movements of the animal, to recognize movements of the animal that are caused by the breathing of the animal. All this can be carried out with the aid of the predetermined algorithm or filter 92. Furthermore, it holds that the computer and/or the control unit according to FIG. 14 is arranged, on the basis of the electronic information about the measured movements $\hat{B}$ of the animal and on the basis of the electronic information about the measured breathing of the animal, to recognize with the aid of the algorithm 94 that the animal is standing still or lying and is breathing with a frequency that is greater than a predetermined value and preferably to generate an alert signal when it has been recognized that the animal is standing still or lying and is breathing with a frequency that is greater than the predetermined value. This is an indication that the animal has stress.

Figure 15:
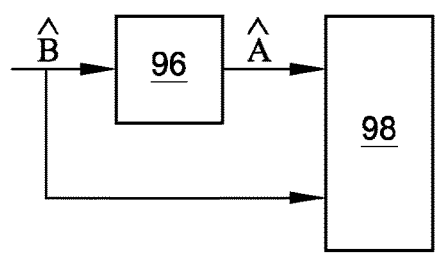

According to FIG. 15 the computer and/or the control unit is arranged, on the basis of the electronic information $\hat{B}$ about the detected movements of the animal, to recognize movements of the animal that are caused by a heart beat of the animal. This can be carried out with a predetermined algorithm or filter 96. By registering the heart beat of an animal in time and analyzing it, it can be established whether the animal is healthy, has stress, and the like.

More particularly, it holds according to FIG. 15 that the computer and/or the control unit is arranged, on the basis of the electronic information about the detected movements of the animal and on the basis of the electronic information about the measured heart beat of the animal, to recognize with the aid of an algorithm or filter 98 that the animal is standing still or lying and has a heart beat that is greater than a predetermined first value and/or has a heart beat that is lower than a predetermined second value. In particular, with the aid of the algorithm or filter 98 an alert signal can then be generated when it has been recognized that the animal is standing still or lying and has a heart beat of a frequency that is greater than the first predetermined value and/or is less than the second predetermined value. The animal can then have stress when the heart beat is greater than the first predetermined value, or be ill when the heart beat is less than the second predetermined value.

Figure 16:
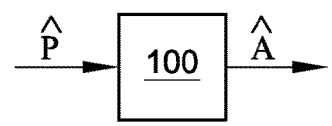

According to FIG. 16 the computer and/or the control unit is arranged to recognize with the aid of an algorithm or filter 100 that the animal is at a position that is not accessible to an animal under normal circumstances and optionally to generate an alert signal when it has been recognized that the animal is at a non-accessible position. If an animal, for example, has escaped, the animal can be promptly caught in this manner.

Figure 17:
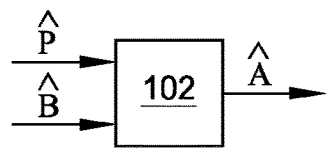

According to FIG. 17 the computer and/or the control unit is arranged to register a behavioral profile of the animal on the basis of the electronic information $\hat{P}$ about a measured position of the animal, and possibly a combination with the electronic information $\hat{B}$ about the detected movements of the animal. This can be carried out with the aid of an algorithm 102.

It is noted that the filters and algorithms discussed with reference to FIGS. 2-17 can be used alone or in any combination in the computer and/or the control unit. The computer and/or the control unit may therefore be arranged for carrying out one or more of these above-mentioned algorithms and/or be provided with one or more of the filters mentioned. The analysis results mentioned may therefore be determined parallel.

It is noted that the positioning means included in the identification unit in this example are communicatively connected with the control unit for feeding electronic information about the position of the identification unit to the control unit. The control unit is arranged to transmit the electronic information about the positions with the aid of the transmitter unit to the receiver unit optionally together with the identification code stored in the identification unit. The movement sensor may be arranged to measure the accelerations, speeds and/or orientations, with 'movements' being understood to mean the speed, acceleration and/or orientation. The identification unit may further be provided with an RFID label 104 which is communicatively connected with the control unit. The RFID label can respond by transmitting an identification code, e.g., an identification code stored in the control unit 8, when it is introduced into an electromagnetic interrogation field, known per se. This electromagnetic interrogation field has a lower frequency than the frequency with which the UHF transmitter 4 transmits. It will be clear that the control unit can have the properties that have been discussed hereinabove for the control unit and/or the computer. This also holds for the computer. In other words, the algorithms mentioned can be carried out by the control unit and by the computer as well as by both, and the filters mentioned can be implemented both in the computer and in the control unit. It will be apparent from the foregoing that the computer and/or the control unit in this example are arranged to interpret the electronic information about detected movements in dependence upon the electronic information about the measured positions. FIGS. 4a, 5, 6, and 7 are examples of this. Also, the computer and/or the control unit is arranged to interpret the electronic information about measured positions in dependence upon the electronic information about the detected movements. FIG. 3 is an example of this. Also, in general, it holds that the computer and/or the control unit is arranged to select on the basis of the electronic information about detected movements and/or on the basis of the electronic information about the measured positions, a predetermined filter and/or a predetermined algorithm with which the electronic information about the measured positions and/or the electronic information about the detected movements is processed. FIGS. 3-7, and FIGS. 12, 14, and 15 are examples of this.

More particularly, it holds that the computer and/or the control unit is provided with a plurality of filters and/or a plurality of algorithms to process the electronic information about the measured positions and/or the electronic information about the detected movements, wherein the computer and/or the control unit is arranged to select, on the basis of the electronic information about the detected movements and/or on the basis of the electronic information about the measured positions, the predetermined filter from the plurality of filters and/or the predetermined algorithm from the plurality of algorithms with which the electronic information about the measured positions and/or the electronic information about the detected movements is processed. When the computer and/or the control unit is arranged to carry out a combination of FIGS. 3-17, that is an example of this. In particular, it holds that the computer and/or the control unit is arranged to select on the basis of the electronic information about the detected movements the predetermined filter and/or the predetermined algorithm for processing electronic information about the measured positions. FIG. 3 is an example of this. Also, it holds in particular that the computer and/or the control unit is arranged to select on the basis of the electronic information about the measured positions the predetermined filter and/or the predetermined algorithm for processing the electronic information about the detected movements. Examples of this are FIGS. 4a, 5 and, for instance, also a combination of these figures which may be implemented in the control unit and/or the computer. Such variants are each understood to be within the scope of the invention. The invention is not in any way limited to the above-outlined embodiments. Thus, the position of the identification unit may also be determined in other manners, as described, for example, in Dutch patent application number 2005776.

The invention claimed is:

1. A system for analyzing a condition of an animal, wherein the system includes at least an identification unit which is arranged to be worn by an animal, wherein the identification unit includes a first transmitter unit, a movement sensor, and a control unit which is communicatively connected with the transmitter unit and the movement sensor, wherein the system further includes a receiver unit and a computer which is connected with the receiver unit and wherein the system further includes positioning means for measuring a position of the identification unit, wherein the movement sensor is different from the positioning means, and wherein the control unit is arranged for, in use, at least one of storing and processing electronic information of movements of the animal which have been obtained with the movement sensor, wherein the receiver unit feeds the received electronic information about at least one of the detected movements and an identification code to the computer, wherein the system is further arranged to feed positions of the identification unit measured with the aid of the positioning means to the computer or the control unit, wherein the system has one of the following four arrangements:

(1) the computer is arranged to process the electronic information about detected movements and electronic information about the measured positions in combination for analyzing the condition of the animal, wherein the computer is provided with a plurality of filters to process the electronic information about at least one of the measured positions and the electronic information about the detected movements, wherein the computer is arranged to select on the basis of at least one of the electronic information about the detected movements and the electronic information about the measured positions the predetermined filter from the plurality of filters with which at least one of the electronic information about the measured positions and the electronic information about the detected movements is processed; or (2) the computer is arranged to process the electronic information about detected movements and electronic information about the measured positions in combination for analyzing the condition of the animal, wherein the computer is provided with a plurality of algorithms to process at least one of the electronic information about the measured positions and the electronic information about the detected movements, wherein the computer is arranged to select on the basis of at least one of the electronic information about the detected movements and the electronic information about the measured positions the predetermined algorithm from the plurality of algorithms with which the electronic information about at least one of the measured positions and the electronic information about the detected movements is processed; or (3) the control unit is arranged to process the electronic information about detected movements and electronic information about the measured positions in combination for analyzing the condition of the animal, wherein the control unit is provided with a plurality of filters to process at least one of the electronic information about the measured positions and the electronic information about the detected movements, wherein the control unit is arranged to select on the basis of at least one of the electronic information about the detected movements and the electronic information about the measured positions the predetermined filter from the plurality of filters with which the electronic information about at least one of the measured positions and the electronic information about the detected movements is processed; or (4) the control unit is arranged to process the electronic information about detected movements and electronic information about the measured positions in combination for analyzing the condition of the animal, wherein the control unit is provided with a plurality of algorithms to process at least one of the electronic information about the measured positions and the electronic information about the detected movements, wherein the control unit is arranged to select on the basis of at least one of the electronic information about the detected movements and the electronic information about the measured positions the predetermined algorithm from the plurality of algorithms with which the electronic information about at least one of the measured positions and the electronic information about the detected movements is processed, and wherein for processing both of the electronic information about detected movements obtained from the movement sensor and the electronic information about the measured positions obtained from the positioning means in combination, the computer or the control unit is arranged to apply a filter or algorithm to process at least a first one of the electronic information about the measured positions and electronic information about the detected movements, and, depending on an outcome of the filter or algorithm, the computer or the control unit is further arranged to process at least a second one of the electronic information about the measured positions and the electronic information about the detected movements to recognize mutually different conditions of the animal, wherein the second one of the electronic information about the measured positions and the electronic information about the detected movements is different from the first one of the electronic information about the measured positions and the electronic information about the detected movements.

2. The system according to claim 1, wherein the computer or the control unit is arranged to interpret the electronic information about detected movements in dependence upon the electronic information about the measured positions.

3. The system according to claim 2, wherein the control unit is arranged such that a frequency with which electronic information about the position of the animal is transmitted by the transmitter unit depends on the electronic information about the detected movements of the animal.

4. The system according to claim 3, wherein the control unit is arranged so as to cause the frequency to be relatively low when the control unit concludes from the electronic information about detected movements that the animal is standing still or lying or to cause the frequency to be relatively high when the control unit concludes from the electronic information about detected movements that the animal is walking.

5. The system according to claim 3, wherein the control unit is arranged so as to cause the frequency to be lowered or raised when the control unit concludes from the electronic information about detected movements that the animal is going to move less or more, respectively.

6. The system according to claim 1, wherein the control unit is arranged to process the electronic information about detected movements and the electronic information about the measured positions in combination, the computer or the control unit is arranged to interpret the electronic information about measured positions in dependence upon the electronic information about the detected movements.

7. The system according to claim 1, wherein the computer or the control unit is arranged to be able to conclude on the basis of the electronic information about the detected movements whether the animal is walking or not walking and to process the electronic information about the measured positions with a first predetermined filter or a first predetermined algorithm if the animal is not walking.

8. The system according to claim 7, wherein the computer or the control unit is arranged such that, in use, the electronic information about the measured positions is integrated with the first predetermined filter or the first predetermined algorithm so that the electronic information is averaged in time.

9. The system according to claim 1, wherein a second predetermined filter is arranged to pass predetermined movements which are associated with rumination or wherein a second predetermined algorithm is arranged to recognize predetermined movements which are associated with rumination.

10. The system according to claim 1, wherein the computer or the control unit is arranged to recognize on the basis of the electronic information about the measured position of the animal that the animal is in a predetermined area in a feeding space and to process the electronic information about the detected movements of the animal with a second predetermined filter or a second predetermined algorithm if it has been recognized that the animal is in the predetermined area in the feeding space, wherein the second predetermined filter is arranged to pass predetermined movements which are associated with eating or wherein the second predetermined algorithm is arranged to recognize predetermined movements which are associated with eating.

11. The system according to claim 10, wherein the computer or the control unit is arranged to register on the basis of the electronic information passed by the second predetermined filter or movements recognized with the second predetermined algorithm at least one of a length of an eating time, number of eating sessions and times at which eating is done.

12. The system according to claim 1, wherein the computer or the control unit is arranged to recognize on the basis of the electronic information about the measured position of the animal that the animal is in a walking space and to process the electronic information about the detected movements of the animal with a second predetermined filter or a second predetermined algorithm if it has been recognized that the animal is in the walking space, wherein the second predetermined filter is arranged to pass predetermined movements which are associated with estrus of the animal or wherein the second predetermined algorithm is arranged to recognize predetermined movements which are associated with estrus of the animal.

13. The system according to claim 12, wherein the computer is arranged to register where the animal is located at a moment that movements are detected in respect of the animal that are associated with estrus of the animal, wherein the computer is further arranged to determine for other animals each also provided with an identification unit when the other animals have been in the neighborhood of the animal in respect of which movements that are associated with estrus of the animal have been detected.

14. The system according to claim 1, wherein the computer or the control unit is arranged to recognize on the basis of the electronic information about the measured position of the animal that the animal is in a calving pen and to process the electronic information about the detected movements of the animal with a second predetermined filter or a second predetermined algorithm if it has been recognized that the animal is in a calving pen, wherein the second predetermined filter is arranged to pass predetermined movements which are associated with calving of the animal or wherein the second predetermined algorithm is arranged to recognize predetermined movements which are associated with the calving of the animal, wherein, the predetermined movement that is associated with calving consists of repeated lying down and getting up again.

15. The system according to claim 1, wherein the computer or the control unit is arranged to recognize on the basis of the electronic information about successive measured positions of the animal and on the basis of the electronic information about the detected movements of the animal whether an animal is taking steps of a length that is less than a predetermined length.

16. The system according to claim 15, wherein the computer or the control unit are arranged to generate an alert signal when the computer or the control unit has recognized a plurality of steps of a length that is shorter than the predetermined length.

17. The system according to claim 1, wherein the computer or the control unit is arranged to recognize on the basis of the electronic information about the measured position of the animal that the animal is in a cubicle and to recognize on the basis of the electronic information about the detected movements of the animal that the animal is lying, wherein the computer or the control unit is arranged to register that the animal is lying when on the basis of the electronic information about the measured positions of the animal it has been recognized that the animal is in the cubicle and on the basis of the electronic information about the detected movements of the animal it has been recognized that the animal is lying.

18. The system according to claim 17, wherein the computer or the control unit are further arranged to register lying times on the basis of the registered information about the lying of the animal, while lying times may be understood to mean the times at which the animal is lying or the length of periods during which the animal is lying.

19. The system according to claim 1, wherein the computer or the control unit is arranged to recognize on the basis of the electronic information about the measured position of the animal that the animal is not in a cubicle and to recognize on the basis of the electronic information about the detected movements of the animal that the animal is lying, wherein the computer or the control unit is arranged to register that the animal is an off-bedding sleeper when on the basis of the electronic information about the measured positions of the animal it has been recognized that the animal is not in the cubicle and on the basis of the electronic information about the detected movements of the animal it has been recognized that the animal is lying.

20. The system according to claim 19, wherein the system is further provided with means of stimulating the animal when the animal has been recognized to be an off-bedding sleeper.

21. The system according to claim 1, wherein the computer or the control unit is arranged to recognize on the basis of the electronic information about the detected movements of the animal that the animal is restless and where the restless animal is then located.

22. The system according to claim 21, wherein the control unit or computer is further arranged to at least one of generate an alert signal when it has been recognized that the animal is restless and to register each time where the animal is located when it is restless.

23. The system according to claim 1, wherein the system is provided with a plurality of identification units which are each arranged to be worn by an animal, wherein the computer or the control unit is arranged to recognize on the basis of the electronic information about the detected movements that a plurality of the animals are restless and where the restless animals are then located.

24. The system according to claim 23, wherein the control unit or the computer is further arranged to at least one of generate an alert signal when it has been recognized that the restless animals are located in each other's vicinity and to register each time where the animals are jointly located when they are restless.

25. The system according to claim 1, wherein the computer or the control unit is arranged to recognize on the basis of the electronic information about the detected movements of the animal that the animal is standing still.

26. The system according to claim 25, wherein the computer or the control unit is arranged to register at least one of when and how long the animal is standing still together with information about where the animal is standing still then.

27. The system according to claim 1, wherein the computer or the control unit is arranged to recognize, on the basis of the electronic information about the detected movements of the animal, movements of the animal that are caused by a breathing of the animal.

28. The system according to claim 27, wherein the computer or the control unit is arranged to recognize on the basis of the electronic information about the measured position of the animal and on the basis of the electronic information about the measured breathing of the animal that the animal is standing still or lying and is breathing with a frequency that is greater than a predetermined value.

29. The system according to claim 28, wherein the computer or the control unit is arranged to generate an alert signal when it has been recognized that the animal is standing still or lying and is breathing with a frequency that is greater than the predetermined value.

30. The system according to claim 1, wherein the computer or the control unit is arranged to recognize, on the basis of the electronic information about the detected movements of the animal, movements of the animal that are caused by a heart beat of the animal.

31. The system according to claim 30, wherein the computer or the control unit is arranged to recognize on the basis of the electronic information about the detected movements of the animal and on the basis of the electronic information about the measured heart beat of the animal, respectively, that the animal is standing still or lying and has a heart beat that is greater than a predetermined first value or a heart beat that is lower than a predetermined second value.

32. The system according to claim 31, wherein the computer or the control unit is arranged to generate an alert signal when it has been recognized that the animal is standing still or lying and has a heart beat with a frequency that is greater than the first predetermined value or less than the second predetermined value.

33. The system according to claim 1, wherein the computer or the control unit is arranged to recognize that the animal is located at a predetermined position that is not accessible to the animal under normal circumstances.

34. The system according to claim 33, wherein the computer or the control unit is arranged to generate an alert signal when it has been recognized that the animal is located at a non-accessible position.

35. The system according to claim 1, wherein the computer or the control unit is arranged to register a behavioral profile of the animal on the basis of the electronic information about measured positions of the animal.

36. The system according to claim 35, wherein the computer or the control unit is arranged to register a behavioral profile of the animal in combination with the electronic information about the detected movements of the animal.

37. The system according to claim 1, wherein the computer or the control unit are provided with a predetermined algorithm to process the electronic information about detected movements and the electronic information about the measured positions in combination for analyzing the condition of the animal.

38. The system according to claim 1, wherein the identification unit is provided with the positioning means, wherein the positioning means is a GPS receiver, which is communicatively connected with the control unit for feeding electronic information about the position of the identification unit to the control unit, wherein the control unit is arranged to transmit electronic information about the positions with the aid of the transmitter unit to the receiver unit.

39. The system according to claim 38, wherein the control unit is arranged to transmit electronic information about the positions together with an identification code which is stored in the identification unit.

40. The system according to claim 1, wherein the positioning means are provided with a plurality of positioning receivers which are set up at mutually different positions, wherein the system is arranged to determine the position of the identification unit on the basis of signals received with the positioning receivers, which have been transmitted with the identification unit.

41. The system according to claim 1, wherein the movement sensor is arranged to measure at least one of accelerations, speeds and orientations, wherein movement is understood to mean a speed, acceleration or orientation.

42. The system according to claim 1, wherein the movement sensor is implemented as an acceleration detector, compass or a gyroscope.

43. The system according to claim 1, wherein the identification unit is further provided with an RFID label which is communicatively connected with the control unit.

44. The system according to claim 1, wherein the control unit is arranged to transmit at least one of electronic information about the detected movements of the animal and an identification code which is stored in the identification unit with the aid of the transmitter unit to the receiver unit.

45. The system according to claim 1, wherein the control unit is also arranged to transmit information about a result of the analysis with the transmitter unit to the receiver unit for at least one of storage and further processing in the computer.

46. The system according to claim 1, wherein the computer or the control unit is arranged to recognize on the basis of the electronic information about the measured positions of the animal that the animal is in a bedded area and to process the electronic information about the detected movements of the animal with a second predetermined filter or a second predetermined algorithm if it has been recognized that the animal is in the bedded area provided that it has additionally been recognized on the basis of the electronic information about the measured movements of the animal that the animal is lying or standing still.

* * * * *